United States Patent [19]

Brooks

[11] Patent Number: 4,785,820

[45] Date of Patent: Nov. 22, 1988

[54] METHOD AND APPARATUS FOR SYSTOLIC BLOOD PRESSURE MEASUREMENT

[75] Inventor: James R. Brooks, Hillsboro, Oreg.

[73] Assignee: SpaceLabs, Inc., Bothell, Wash.

[21] Appl. No.: 944,892

[22] Filed: Dec. 22, 1986

[51] Int. Cl.[4] ............................................. A61B 5/02
[52] U.S. Cl. ..................................................... 128/681
[58] Field of Search .............................. 128/680–683; 364/415–417

[56] References Cited

U.S. PATENT DOCUMENTS 4,313,445 2/1982 Georgi ................................. 128/680
4,638,810 1/1987 Ramsey, III et al. .......... 128/682 X Primary Examiner—Francis J. Jaworski
Attorney, Agent, or Firm—Seed and Berry

[57] ABSTRACT

A method and apparatus for smoothing raw oscillometric table data in the region around systolic blood pressure to reduce respiration interference is disclosed. Systolic blood pressure is determined by averaging intermediate systolic pressures calculated in association with dual thresholds instead of a single threshold. Interpolation is used between adjacent applied cuff pressure values having table entries located on either side of each of the upper and lower threshold values. Normalization of the table is employed to improve interpolation resolution.

4 Claims, 4 Drawing Sheets

METHOD AND APPARATUS FOR SYSTOLIC BLOOD PRESSURE MEASUREMENT

BACKGROUND OF THE INVENTION

The present invention relates to blood pressure measurement, in particular to a method and apparatus for the measurement of systolic blood pressure.

In most automatic indirect methods of blood pressure measurement, a pressure cuff is attached to a patient's arm adjacent a blood vessel, the cuff is pressurized with an applied pressure which is high enough to occlude the blood vessel and the applied pressure is gradually reduced. As the pressure is reduced to below systolic and then diastolic, blood begins to flow through the blood vessel creating the well known Korotkoff sounds and pulsatile pressures in the blood vessel. The sounds can be detected by a microphone at pulsatile pressures by a pressure transducer. The sensor, whether a microphone or pressure transducer, measures a quantity which is representative of the patient's blood pressure.

An oscillometric table is then formed of values of the quantity measured at various applied pressures as the applied pressure is gradually changed. Using the table the systolic and diastolic blood pressures are determined.

In a well behaved reading of blood pressure, the values generally increase from low values at applied pressures above the systolic to a maximum value at applied pressures between systolic and diastolic. Similarly, the values generally increase from low values at applied pressures less than diastolic to the maximum values. Respiration of the patient and other artifacts often cause the table to be non-monotonic. For example, respiration of the patient can change the instantaneous blood pressure by as much as forty millimeters of mercury. Effects of respiration on blood pressure are usually worse with people with compromised respiration and tends to be more pronounced at higher applied cuff pressures at or around systolic blood pressure levels.

Respiration then can affect the accuracy of blood pressure measurement particularly where a single threshold algorithm is applied to the oscillometric table in order to determine systolic blood pressure. Means for eliminating or minimizing the effects of respiration on the accuracy of measurement of systolic blood pressure is desireable.

SUMMARY OF THE INVENTION

An improved apparatus and method for determining systolic blood pressure from the non-invasive oscillometric system of measuring blood pressure is provided. Systolic blood pressures are determined for two threshold levels on either side of a level substantially about 50 percent of the maximum oscillation in the table. These two systolic values are then averaged to find the final systolic blood pressure.

Interpolation between adjacent applied pressure levels having oscillometric values associated therewith on either side of each of the dual threshold levels is provided, as is normalization of the oscillometric table to improve interpolation resolution.

DETAILED DESCRIPTION OF THE DRAWINGS

Figure 1:
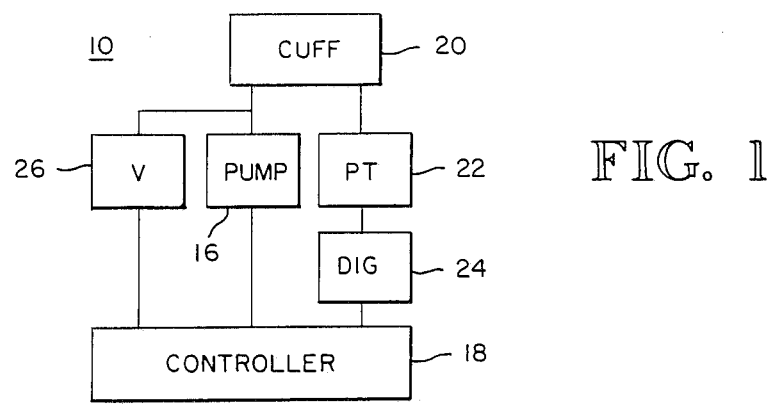
FIG. 1 is a block diagram of an apparatus for the indirect measurement of blood pressure.
Figure 2:
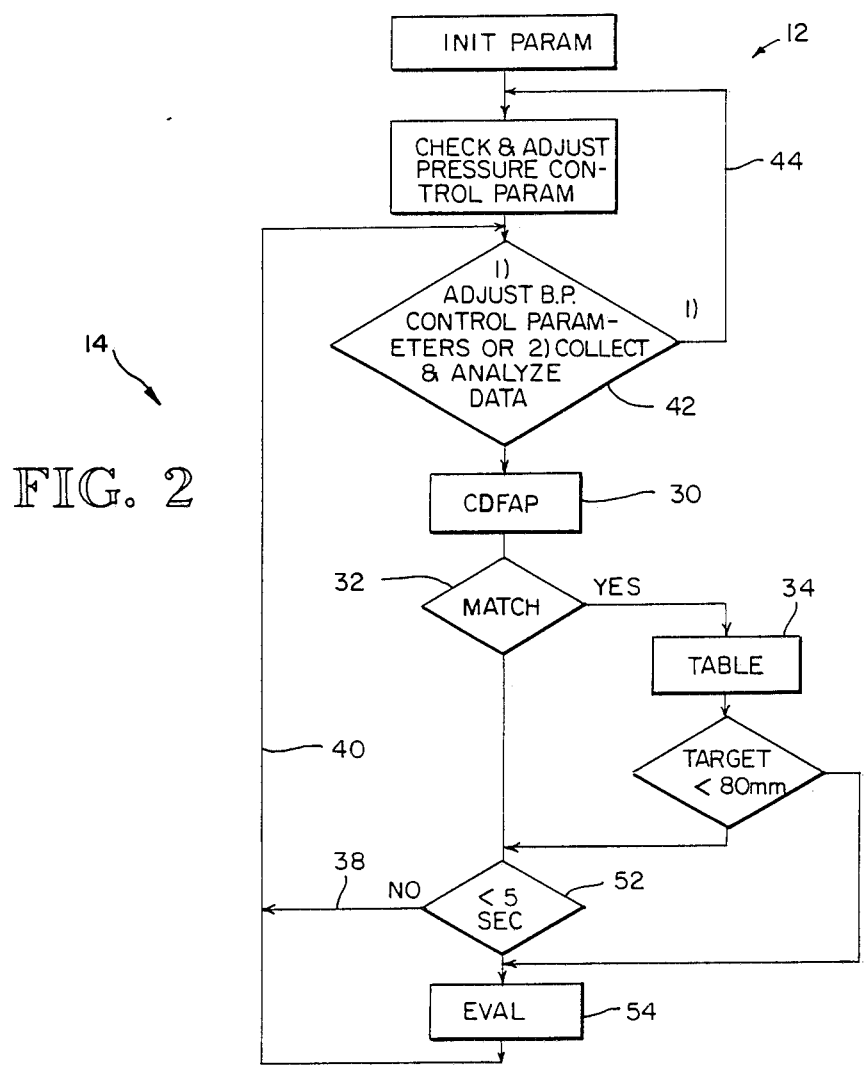
FIG. 2 is a block diagram flow chart of the overall operation of the apparatus of FIG. 1.
Figure 3:
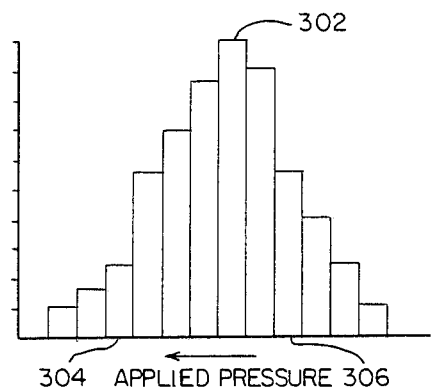
FIG. 3 is a graphic representation of a table of well behaved values formed during the operation of the blood pressure measurement of FIG. 1.

Referring now to the figures, the system designated generally 10 in FIG. 1 operates in basically two loops, a blood pressure control loop 12 (bp loop) and a collect and analyze data loop 14 (cd loop) in FIG. 2. Initially, a pump 16 under the control of a controller 18 in the bp loop 12 pumps up the pressure in a cuff 20 located on the patent's arm to a predetermined level, e.g. 165 millimeters (mm) of mercury. A pressure transducer 22 senses the applied pressure in the cuff and any variations due to pressure pulses in the arm's artery due to the beating of the heart. The electrical output signal from the transducer is sampled and digitized in digitizer 24 and the samples sent to the controller 18 for processing. The gain and dynamic range of the signals are checked and adjusted at this time as well. The cd loop 14 is exercised by the controller 18 on the digital data collected so far, and when completed the bp loop 12 again takes over and bleeds pressure from the cuff 20 through a valve 26 under the control of the controller 18. The pressure each time is bled down in predetermined increments, e.g., 4 or 6 or 8 mm. At each applied pressure level, the collect and analyze data loop 14 is exercised to obtain an oscillometric amplitude value representative of pulsatile pressure in the blood vessel occuring at that particular applied pressure step. FIG. 3 shows an ideal bar graph showing the normalized values of the peaks of the oscillometric variations at each of the applied cuff pressure steps. The table shows a clearly defined single maximum value 302 and clearly defined systolic and diastolic pressures 304 and 306, respectively.

When in the collect and analyze data loop 14, the system first collects data for a peak of the oscillometric variations at a chosen applied pressure level 30. Samples of the variations are provided every millisecond and their amplitudes are checked until a peak amplitude is determined. This process takes about 150 milliseconds before a peak is formed. The peak is compared with the previous peak measured for the same applied blood pressure level. If a match occurs 32, the value of the peak is entered into an oscillometric value table 34. If no peak is found, zero is entered. If two peaks don't match, the search continues until a match occurs. This procedure helps to eliminate artifacts due to noise, patient movement, etc. Typically, a match is found in about 2 heart beats. If no match is formed in 2 seconds, a zero is placed in the table and the cuff is bled to the next cuff pressure.

The system then returns to the blood pressure control loop via line 38, 40, decision box 42 and line 44 where the applied pressure is bled down one more step and the process to find and match a peak and enter the value into the table is repeated.

Eventually either the applied pressure will fall below a predetermined level 50 or the length of time for which the cuff has been pressurized will approach a predetermined interval 52. In either case this triggers the system to evaluate the table to see if a determination of systolic and diastolic pressures can be made from the table 54. In the preferred embodiment the predetermined applied pressure is 80 mm and the predetermined time duration of cuff pressurization is within 5 seconds of a 116 second time out criteria. If systolic and diastolic pressure calculations are unobtainable by the end of 116 seconds, the blood pressure control loop bleeds down the cuff pressure to zero.

Prior art methods of determining systolic blood pressure from oscillometric tables include selecting a single oscillometric threshold value for the table and selecting the applied cuff pressure from the table at or near the single threshold value on the higher applied cuff pressure side of the peak oscillometric value in the table. Fifty percent of maximum is an example of a single threshold value used by some blood pressure equipment manufacturers.

Figure 6:
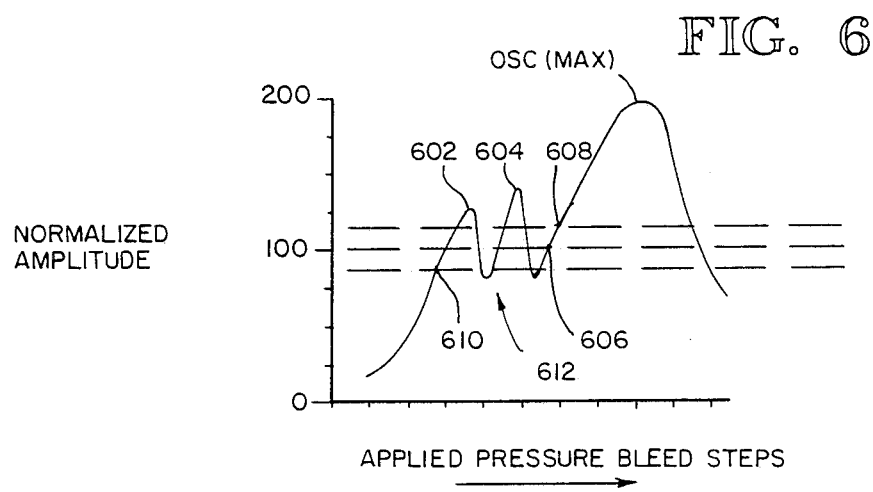
FIG. 6 is a curve defined by the oscillometric table showing the presence of respiration interference.

It has been discovered, however, that respiration, especially, in those with compromised respiration, causes changes in instantaneous blood pressure readings, particularly in the region around the fifty percent threshold. See the peaks 602 and 604 in FIG. 6. If one were to look at a 50 percent threshold on the curve of FIG. 6 it would cross the curve at five places causing ambiguities. One prior art algorithm would pick the crossing closest to OSC(MAX). See the x 606 in FIG. 6. It comprises using a dual threshold to measure systole with the lower threshold below fifty percent and the upper threshold above fifty percent. In the preferred embodiment, the lower threshold is substantially at 44 percent of the maximum oscillometric value (OSC(MAX)) in the table and the upper threshold is substantially at 56 percent of OSC(MAX).

Figure 4:
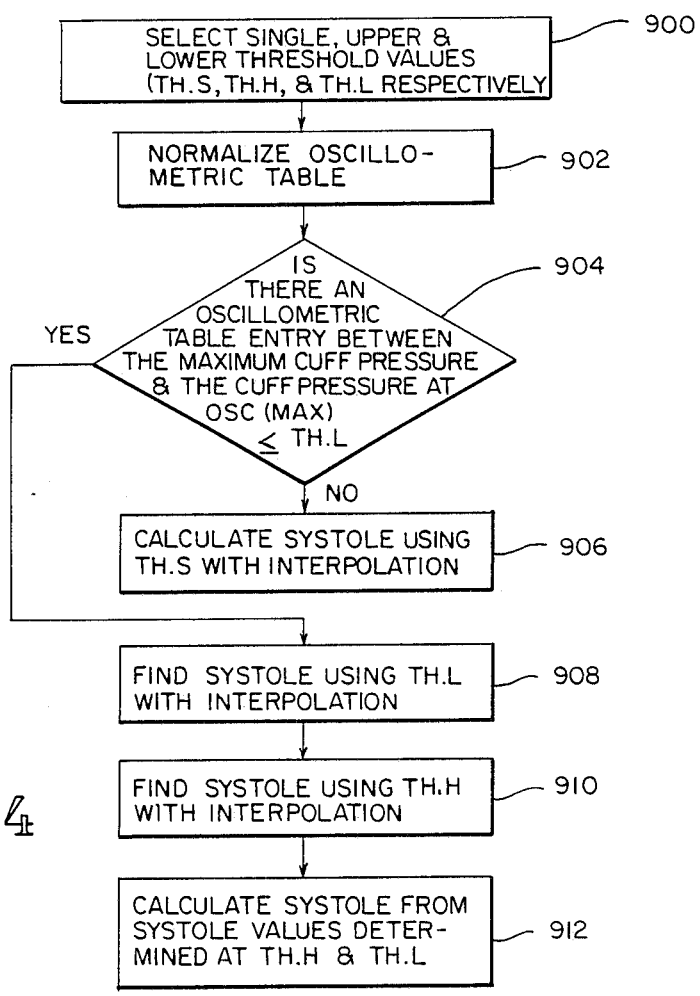
FIG. 4 is a block diagram flow chart for determining systolic blood pressure from the oscillometric table.

The following table of definition of terms will be helpful in connection with the description of FIG. 4.

TABLE

TH.L = lower threshold used in determination of systole

OSC(L) = amplitude of first oscillometric peak less than or equal to the lower threshold scanning from mean to higher cuff pressures.

CUFF(L) = cuff pressure corresponding to OSC(L)

CUFF(L=1) = the cuff pressure at the bleed step above CUFF(L)

OSC(L=1) = amplitude of the oscillometric peak collected at CUFF(L=1)

SYS(L) = interpolated systolic determined at threshold TH.L.

TH.H = upper threshold used in determination of systole

OSC(H) = amplitude of first oscillometric peak less than or equal to the upper threshold scanning from mean to higher cuff pressures CUFf(H) = cuff pressure corresponding to OSC(H)

CUFF(H+1) = the cuff pressure at first bleed step above CUFF(H)

OSC(H+1) = amplitude of the oscillometric peak collected at CUFF(H+1)

OSC(MAX) = amplitude of the largest oscillometric peak collected.

TH.S = single threshold used in determination of systole

OSC(S) = amplitude of first oscillometric peak less than or equal to the single threshold scanning from mean to higher cuff pressures.

CUFF(S) = cuff pressure corresponding to OSC(S)

CUFF(S+1) = the cuff pressure at the bleed step above CUFF(S)

OSC(S+1) = amplitude of the oscillometric peak collected at CUFF(S+1)

SYS(S) interpolated systolic determined at threshold TH.S.

Referring now to FIG. 4, the preferred manner of determining systolic blood pressure from the oscillometric table is disclosed. After selecting single, upper and lower threshold values 900 such as those described above, the oscillometric table is normalized 902 to improve interpolation resolution, interpolation being described in more detail below. To normalize, a new amplitude for each value in the table is calculated as follows:

new amplitude = (old amplitude *200)/ OSC(MAX)

Next, the oscillometric table is examined 904 to see if there is an oscillometric table entry with a value at or below the lower threshold. If there is no such entry, then, using a single threshold value, e.g. 50 percent, systole is determined 906. Interpolation between applied cuff pressures corresponding to oscillometric table values on either side of TH.S is performed as described within the brackets in the equation below.

$$SYS(S) = CUFF(S) - \frac{[TH \cdot S - OSC(S)]}{[OSC(S + 1) - OSC(S)]} * [CUFF(S) - CUFF(S + 1)]$$

Figure 5:
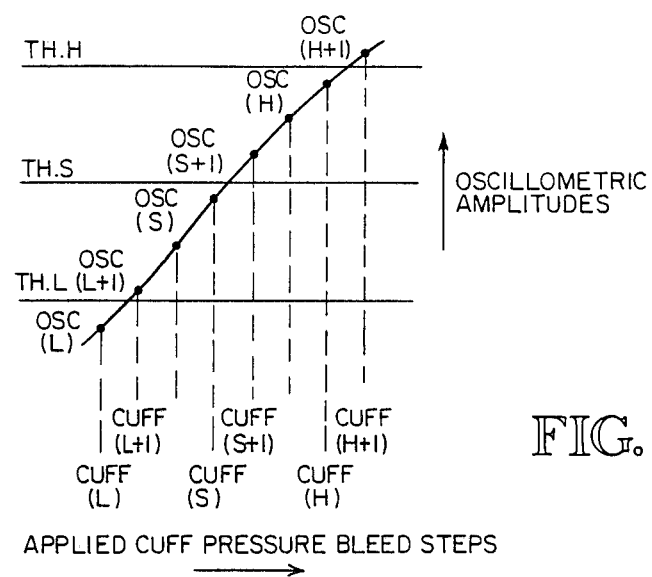
FIG. 5 is a diagram showing the relationship of various table threshold values and corresponding table values and applied cuff pressures used in the interpolation of systole.

The relationship existing between the parameters shown in the above equation relative to the oscillometric table values and applied cuff pressure steps is shown in FIG. 5.

If, on the other hand, a table value less than the lower threshold value exists, then the dual thresholds, TH.H and TH.L will be used to determine systole. First, systole for the lower threshold using interpolation will be determined 908. This is done by finding the first oscillometric amplitude from the table which is less than or equal to TH.L, scanning the table from OSC(MAX) to higher cuff pressures. Then the following equation with interpolation is used to find systole at TH.L:

$$SYS(L) = CUFF(L) - \frac{[TH \cdot L - OSC(L)]}{[OSC(L + 1) - OSC(L)]} * [CUFF(L) - CUFF(L + 1)]$$

Next, systole is calculated for the upper threshold value 910. The first oscillometric table value less than or equal to TH.H is found, scanning from OSC(MAX) to higher cuff pressures. The following equation used will interpolate between adjacent cuff values is used to calucate systole:

$$SYS(H) = CUFF(H) - \frac{[TH \cdot H - OSC(H)]}{[OSC(H + 1) - OSC(H)]} * [CUFF(H) - CUFF(H + 1)]$$

A final value for systole is determined 912 be averaging SYS(H) and SYS(L):

$$SYSTOLE = [SYS(H) + SYS(L)]/2$$

The x marked 606 represents the value of systole which would be determined from at least one prior art method using the oscillometric method. The x marked 608 is SYS(H), while the x marked 610 is SYS(L). SYSTOLE as determined from the average of SYS(H) and SYS(L) is between SYS(H) and SYS(L) as indicated by arrow 612.

What is claimed is:

1. A method for measuring systolic blood pressure, comprising the steps of:
   attaching a pressure cuff to a patient adjacent to a blood vessel;
   pressurizing the cuff sufficiently to occlude the blood vessel;
   alternately measuring counter pressure pulses in the cuff and decrementing the cuff pressure;
   forming a table of raw, unsmoothed data measurements from the measured counter pressure pulses corresponding to the decremented cuff pressure;
   selecting an upper systolic threshold limit and a lower systolic threshold limit on either side of approximately 50% of a maximum measured counter pressure;
   scanning the table from the maximum measured counter pressure towards larger corresponding cuff pressures and finding a first measured counter pressure less than the lower systolic threshold, a first measured counter pressure greater than the lower systolic threshold and interpolating therebetween to arrive at a lower threshold result;
   associating the lower threshold result with a lower systolic pressure;
   scanning the table from the maximum measured counter pressure towards larger corresponding cuff pressures and finding the first measured counter pressure less than the upper systolic threshold, a first measured counter pressure greater than the upper systolic threshold and interpolating therebetween to arrive at an upper threshold result;
   associating the upper threshold result with an upper systolic pressure; and
   averaging the upper and lower systolic pressure to arrive at a systolic pressure, whereby an accurate systolic pressure is obtained from raw, unsmoothed measured counter pressure data, even including random respiration artifacts, without smoothing the raw data.

2. The method of claim 1, wherein the upper and lower systolic threshold are 56% and 44%, respectively.

3. An apparatus for measuring systolic blood pressure, comprising the steps of:
   means for attaching a pressure cuff to a patient adjacent to a blood vessel;
   means for pressurizing the cuff sufficiently to occlude the blood vessel;
   means for alternately measuring counter pressure pulses in the cuff and decrementing the cuff pressure;
   means for forming a table of raw, unsmoothed data measurements from the measured counter pressure pulses corresponding to the decremented cuff pressures;
   means for selecting an upper systolic threshold limit and a lower systolic threshold limit on either side of approximately 50% of a maximum measured counter pressure;
   means for scanning the table from the maximum measured counter pressure towards larger corresponding cuff pressures and finding a first measured counter pressure less than the lower systolic threshold, a first measured counter pressure greater than the lower systolic threshold and interpolating therebetween to arrive at a lower threshold result;
   means for associating the lower threshold result with a lower systolic pressure;
   means for scanning the table from the maximum measured counter pressure towards larger corresponding cuff pressures and finding a first measured counter pressure less than the upper systolic threshold, a first measured counter pressure greater than the upper systolic threshold and interpolating therebetween to arrive at an upper threshold result;
   associating the upper threshold result with an upper systolic pressure; and
   means for averaging the upper and lower systolic pressure to arrive at a systolic pressure, whereby an accuratesystolic pressure is obtained from raw, unsmoothed measured counter pressure data, even including random respiration artifacts, without smoothing the raw data.

4. The apparatus of claim 1, wherein the upper and lower threshold are 56% and 44%, respectively.

* * * * *